(12) United States Patent
Clare et al.

(10) Patent No.: US 7,204,821 B1
(45) Date of Patent: Apr. 17, 2007

(54) SURGICAL FLUID MANAGEMENT SYSTEM WITH SUCTION CONTROL

(75) Inventors: Christopher R. Clare, Los Altos Hills, CA (US); Steve Griffiths, Ellicott City, MD (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/495,005

(22) Filed: Jan. 31, 2000

(51) Int. Cl.
*A61M 1/00* (2006.01)
*A61M 31/00* (2006.01)
*G05D 17/36* (2006.01)

(52) U.S. Cl. .......... 604/30; 604/67; 137/102; 137/625.47

(58) Field of Classification Search .......... 137/625.47, 137/624.14, 597, 636.3; 604/505, 43, 37, 604/247, 67, 493, 147, 30, 22, 65, 245, 320, 604/319, 35, 276; 606/200, 2; 514/449; 128/207.14
See application file for complete search history.

(56) References Cited

U.S. PATENT DOCUMENTS

| | | | | |
|---|---|---|---|---|
| 3,833,018 A | * | 9/1974 | Brooks | 137/625.4 |
| 4,108,207 A | * | 8/1978 | Doody | 137/614.17 |
| 4,312,341 A | | 1/1982 | Zissimopoulos et al. | |
| 4,344,429 A | | 8/1982 | Gupton et al. | |
| 4,399,711 A | | 8/1983 | Klein | |
| 4,594,533 A | | 6/1986 | Snook et al. | |
| 4,796,583 A | | 1/1989 | Nagasaka et al. | |
| 4,810,242 A | * | 3/1989 | Sundblom et al. | 604/119 |
| 4,816,695 A | * | 3/1989 | Lavin | 250/573 |
| 4,819,694 A | * | 4/1989 | Jiang | 137/625.47 |
| 5,045,077 A | | 9/1991 | Blake, III | |
| 5,052,341 A | * | 10/1991 | Woolford et al. | 119/14.17 |
| 5,419,766 A | | 5/1995 | Chang et al. | |
| 5,741,237 A | | 4/1998 | Walker | |
| 6,149,627 A | | 11/2000 | Uber, III | |
| 6,149,633 A | | 11/2000 | Maaskamp | |
| 6,152,902 A | | 11/2000 | Christian et al. | |
| 6,206,014 B1 | | 3/2001 | Cameron, III et al. | |
| 6,283,937 B1 | * | 9/2001 | Takamatsu et al. | 604/31 |

FOREIGN PATENT DOCUMENTS

| | | |
|---|---|---|
| WO | WO 96 05873 | 2/1996 |
| WO | WO 98 55164 A | 12/1996 |
| WO | 9716220 | 5/1997 |

* cited by examiner

*Primary Examiner*—Michael J. Hayes
*Assistant Examiner*—Roz Maiorino (57) ABSTRACT

Apparatus for controlling the volume of surgical fluid present in a cavity in the body of a patient during surgery includes a conduit to the cavity for conducting the surgical fluid therefrom to at least one receptacle for receiving the fluid from said cavity. A source of vacuum assists in withdrawing fluid from the cavity and a vacuum controller interposed between the vacuum source and the receptacle controls the duration of time the receptacle is exposed to vacuum from the vacuum source. The apparatus preferably has a vacuum sensor for sensing vacuum levels in the receptacle when disconnected from the source of vacuum and shares the source of vacuum with another application, giving priority to maintaining a proper vacuum level in the receptacle.

11 Claims, 13 Drawing Sheets

SURGICAL FLUID MANAGEMENT SYSTEM WITH SUCTION CONTROL

FIELD OF THE INVENTION

The present invention relates to medical procedures and devices, more particularly to those devices used to infuse and remove fluids from the body of a patient during a surgical procedure.

BACKGROUND OF THE INVENTION

Endoscopic/laproscopic surgical procedures have grown significantly in popularity over the years due to the fact that they are minimally invasive and the miniature, remotely-controlled surgical instruments used have improved. To allow such procedures to be undertaken, means are frequently required to distend the patient's body cavity at the site of surgery to allow for surgical implement manipulation and visualization. Gasous or liquid insulflatants are used for this purpose depending upon the operation. Certain procedures also utilize a liquid insulflatant as a lavage for removing blood and excised tissue from the surgical site to maintain visibility and to clean the area. For example, in fibroid removal, the uterus is flooded with a clear liquid, e.g., isotonic saline solution, under sufficient pressure to separate the walls of the uterus to permit the surgical site to be viewed with an endoscope. After the uterine cavity has been distended by the liquid, a surgical tool such as an electrocautery tool or resectoscope, may be positioned within the uterus to remove the fibroids which are vaporized at its cutting surface. During the surgery, fluid flow out of the uterus is maintained and the severed tissue and electro surgical debris are removed from the uterus with the outflowing fluid. During procedures of this type, the amount of irrigating liquid present in the patient's body must be closely controlled because excessive absorption thereof can be extremely detrimental to the patient. Accordingly, inflow to the body cavity must closely approximate outflow. In certain instances, a pressure differential is provided in order to maintain distension of the cavity. Many fluid management systems utilize a source of vacuum to control fluid outflow. Various methods have been proposed in the past to monitor the fluid inflow and outflow in surgical fluid management systems, but there is a continuing need for ever improved precision in the management of fluid flow in these applications. Accordingly, an object of the present invention is to provide for simpler, more accurate and more reliable fluid flow control during surgical procedures.

SUMMARY OF THE INVENTION

The problems and disadvantages associated with conventional techniques and devices for controlling the volume of surgical fluid present in a cavity of the body during surgery are overcome by the present invention which includes a conduit to the cavity for conducting the surgical fluid therefrom into at least one receptacle for receiving the fluid from the cavity. A source of vacuum assists in withdrawing fluid from the cavity and a vacuum controller interposed between the vacuum source and the receptacle controls the duration of time the receptacle is exposed to vacuum from the vacuum source.

BRIEF DESCRIPTION OF THE SEVERAL VIEWS OF THE DRAWING

For a better understanding of the present invention, reference is made to the following detailed description of an exemplary embodiment considered in conjunction with the accompanying drawings, in which.

DETAILED DESCRIPTION OF THE PREFERRED EMBODIMENTS

Figure 1:
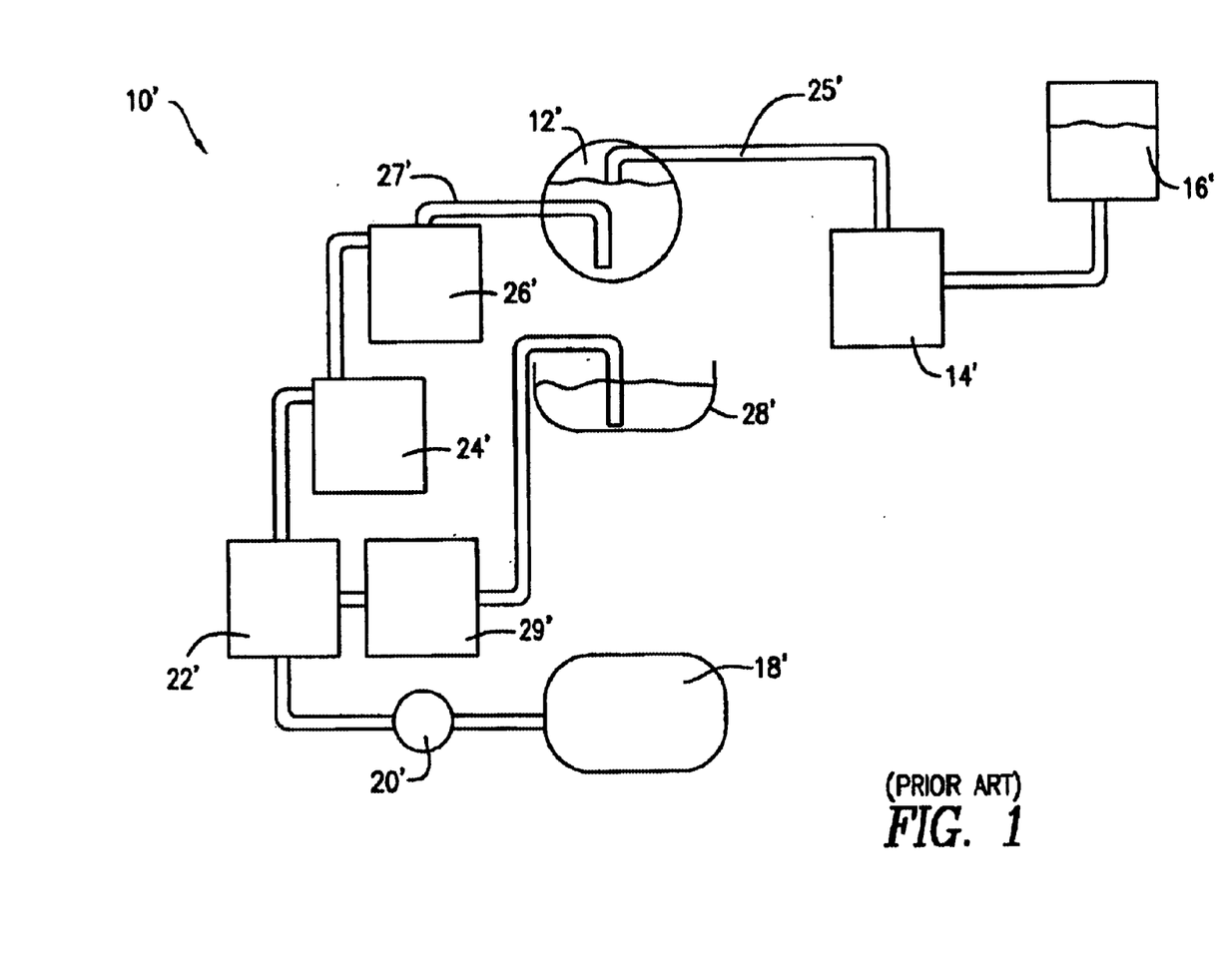
FIG. 1 is a schematic diagram of a fluid management system as known in the prior art.

FIG. 1 shows a fluid management system 10' in accordance with the prior art and includes those components necessary to simultaneously fill and drain a body cavity 12', such as the uterus, with a liquid for distending the body cavity. The liquid may also be used for removing surgical debris, blood and exudate from the cavity 12' during surgery via a continuous flow into and out of the cavity 12'. The fluid is pumped to the cavity 12' by a pump 14' which is fed by a suitable reservoir 16' of sterile fluid, such as isotonic saline solution. Fluid pumped to the cavity 12' fills and distends it to facilitate performing a surgical procedure therein. A vacuum source 18' provides suction under the control of a vacuum regulator 20' to aid in withdrawing fluid from the cavity 12'. The regulator 20' acts through a flow-back filter 22' which prevents fluid withdrawn from the cavity 12' from flowing into the vacuum regulator 20' or the vacuum source 18'. The foregoing arrangement is used to establish a constant flow of fluid to and from the cavity 12' and thereby establishes an equilibrium fluid level and pressure in the cavity 12'. On the vacuum side of the fluid management system 10', a plurality of receptacles 24', 26' may be provided to receive waste fluid that has been withdrawn from the cavity 12'. Typically, these fluid receptacles are arranged in series and provide some convenient and sanitary method and apparatus for disposal of the wasted surgical fluid, such as by using removable plastic liners and the like. Given that there is a positive fluid pressure present in the cavity 12' for distending the walls of the cavity 12' and that neither the inlet fluid conduit 25' or the suction fluid conduit 27' is perfectly sealed, some fluid leakage is to be expected and is collected in a surgical drape system 28'. The drape system 28' is drained of surgical fluid by the vacuum system 18', 20', 22', which draws it into fluid receptacle 29'. Because the fluid retention levels in the patient are critical, the fluid management system described must maintain an acceptable equilibrium fluid volume and pressure in the cavity 12'. As can be appreciated, this requires close monitoring and control of the pump 14' that delivers fluid to the cavity 12', as well as the vacuum 18' which withdraws surgical fluid to waste.

Figure 2:
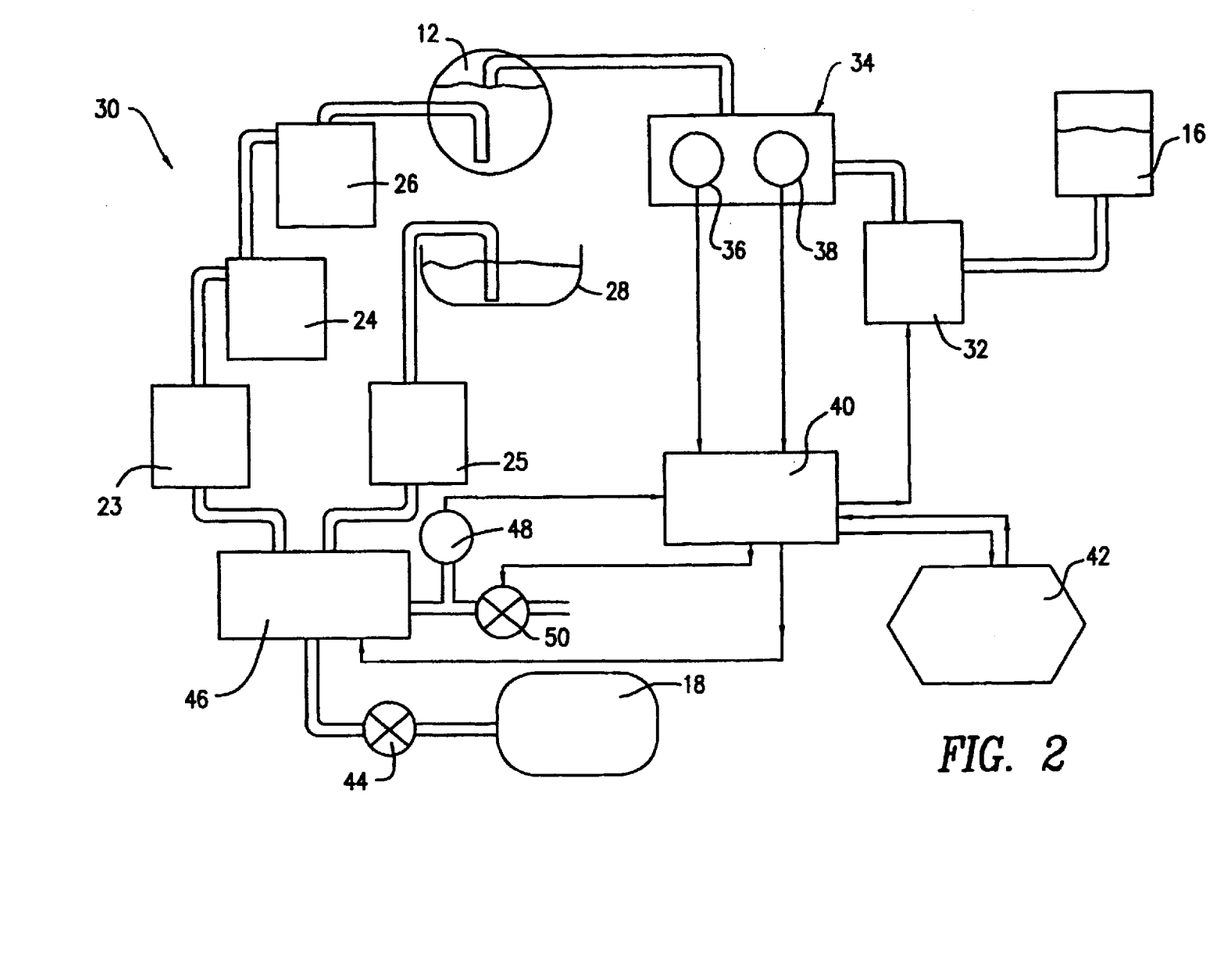
FIG. 2 is a schematic view of a fluid management system in accordance with the present invention.

In FIG. 2, the present invention is shown to include a fluid management system 30 having a pump 32 preferably controlled by a feedback control loop as described below. Fluid is drawn from the reservoir 16 and pumped through a flow dampener 34 which smooths the output pressure variations of the pump 32. Pump 32 is typically a peristaltic type pump utilizing a plurality of rollers that sequentially compress a tube to impart motion to the fluid while preserving sterility of the fluid. The flow dampener 34 preferably includes a pressure sensor 36 for sensing pressure within the flow dampener 34 and a flow sensor 38 to sense the presence of fluid passing through the flow dampener 34. Both sensors 36, 38 preferably communicate their data output to a microprocessor controller 40 that may then utilize that sensor information to control the speed and/or cycle time of the pump 32. Alternatively, pressure and flow data may be displayed on a visual indicator to cue an operator to adjust the pump 32. As yet another alternative, the pump 32 may be equipped with its own pressure sensing probe and pressure responsive controller as more fully described in reference to FIG. 4. A user interface 42 is preferably provided which may include a monitor to display the pressure and flow sensed by the pressure sensor 36 and flow sensor 38, as well as the present output volume of the pump 32. The user interface 42 would typically also include a keyboard or other input device for setting the parameters of system 30 operation.

On the suction side of the system, a plurality of receptacles 24, 26 receive the waste fluid from the cavity 12 for temporary storage and disposal. A flow-back filter 23 is provided in the vacuum line drawing fluid from the cavity 12 and a separate flow-back filter 25 is provided in the drape vacuum line. A regulator valve 44, which may be manually or automatically controlled by the controller 40, controls the presence of vacuum on the vacuum side of the system by connecting or disconnecting with the vacuum source 18. Vacuum present when the valve 44 is open is regulated by the vacuum controller 46 which will be described further below. The vacuum controller 46 acts in cooperation with a vacuum sensor 48 and a vent valve 50 to provide the appropriate amount of vacuum required to maintain the desired fluid level and pressure in the cavity 12, given the inflow established by the pump 32. The vacuum sensor 48 preferably provides vacuum data to the controller 40 which then controls the operation of the vacuum controller 46 and vent valve 50, e.g., by varying the time that vacuum is applied to the flow-back filters 23 and 25 as shall be described further below.

Figure 3:
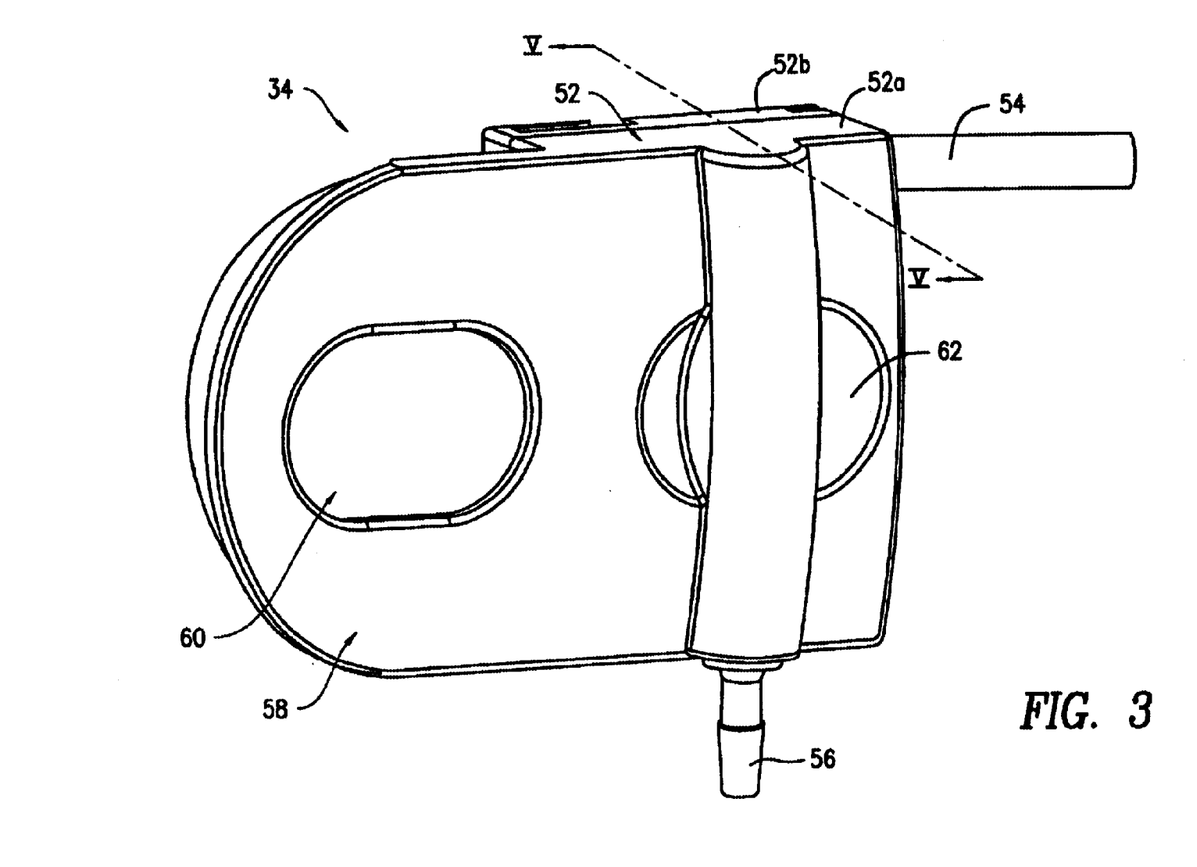
FIG. 3 is a front perspective view of a flow dampener in accordance with the present invention.

FIG. 3 shows the flow dampener 34 having a pressure chamber 52 which is supplied with fluid by inlet tube 54. Fluid exiting the pressure chamber 52 does so via outlet fitting 56. The pressure chamber 52 is formed by joining a pair of hollow mating members 52a and 52b and includes on the face thereof an indentation 62 to enable the user thereof to grip the flow dampener 34. Distal to the pressure chamber 52, the flow dampener 34 has a coupling plate 58 and a rotor opening 60 that enables the dampener to be fitted to a standard peristaltic pump as can be appreciated more fully in reference to FIGS. 4 and 6.

Figure 4:
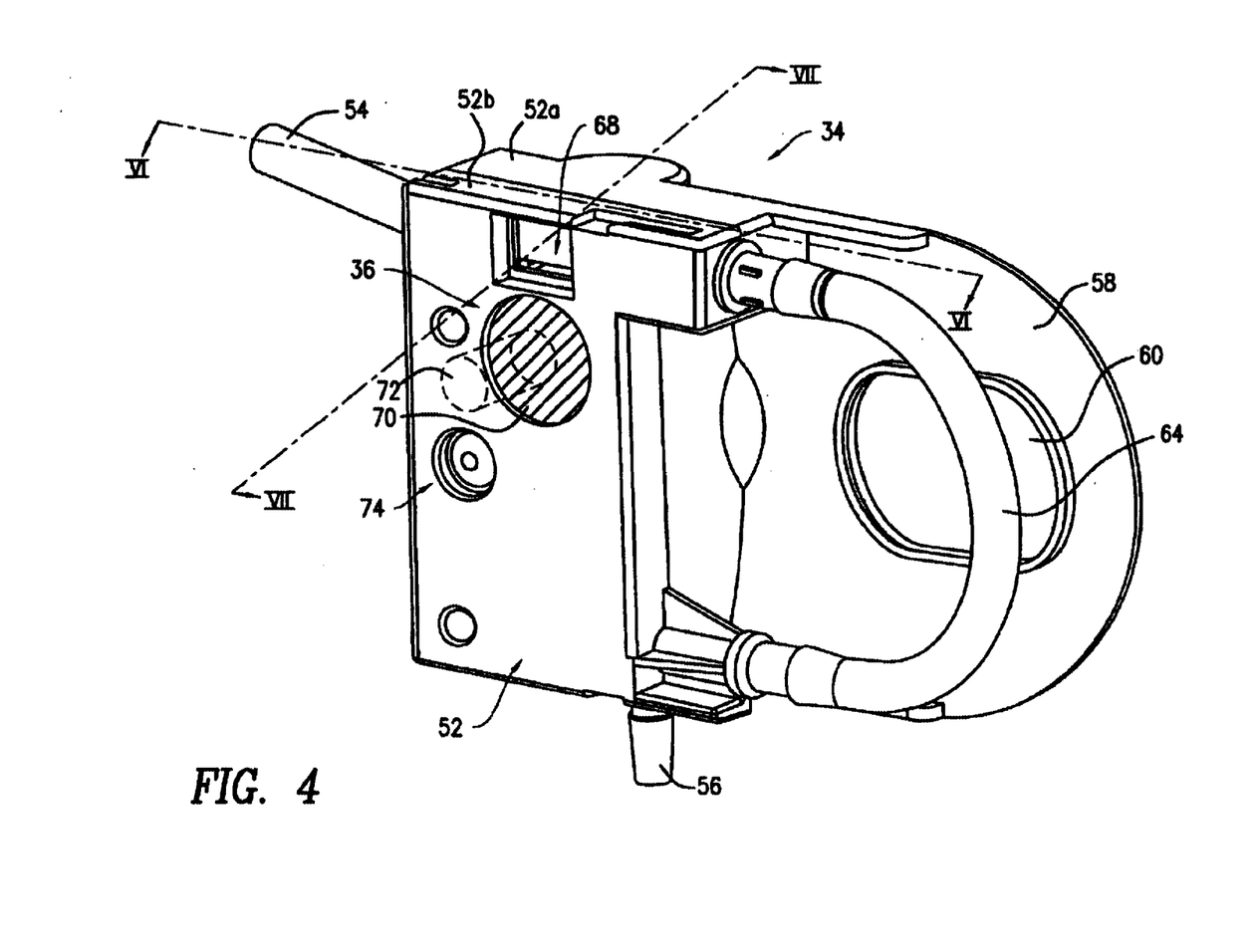
FIG. 4 is a rear perspective view of the flow dampener of FIG. 3.

Referring to FIG. 4, the flow dampener 34 includes a tubing section 64 having a u-shaped configuration that communicates with the inlet tube 54. The u-shaped section 64 interacts with the rollers 66 of a peristaltic pump, as shown diagrammatically in FIG. 6. A window 60 permits the rollers 66 to engage tubing 64. In the embodiment in FIG. 4, the pressure sensor 36 includes a pressure sensing diaphragm 70 that is distended or displaced outwardly by pressure internal to pressure chamber 52. The external distension of the pressure sensing diaphragm 70 is sensed by a pressure probe shaft 72 associated with the peristaltic pump to which the dampener 34 is fitted. The sensed pressure is used for controlling the motor of the pump to maintain a particular pressure automatically, viz., if sensed pressure drops below the setpoint, the pump 32 is turned on. If sensed pressure exceeds the setpoint, the pump 32 is turned off. The foregoing pressure sensing and control feedback arrangement operates either in isolation or in cooperation with the digital controller 40 of FIG. 2.

A fluid detection window 68 is provided in an upper portion of the pressure chamber shell 52b proximate to the inlet tube 54 which is preferably clear or light transmissive material. The fluid detection window 68 is utilized with an optical sensor described further below for determining if fluid fills the inlet tube 54. The pressure chamber 52 has an air vent 74 that is used to vent the chamber 52 of excess air and to allow the fluid to rise to a specific level within the chamber 52, as described further below.

Figure 5:
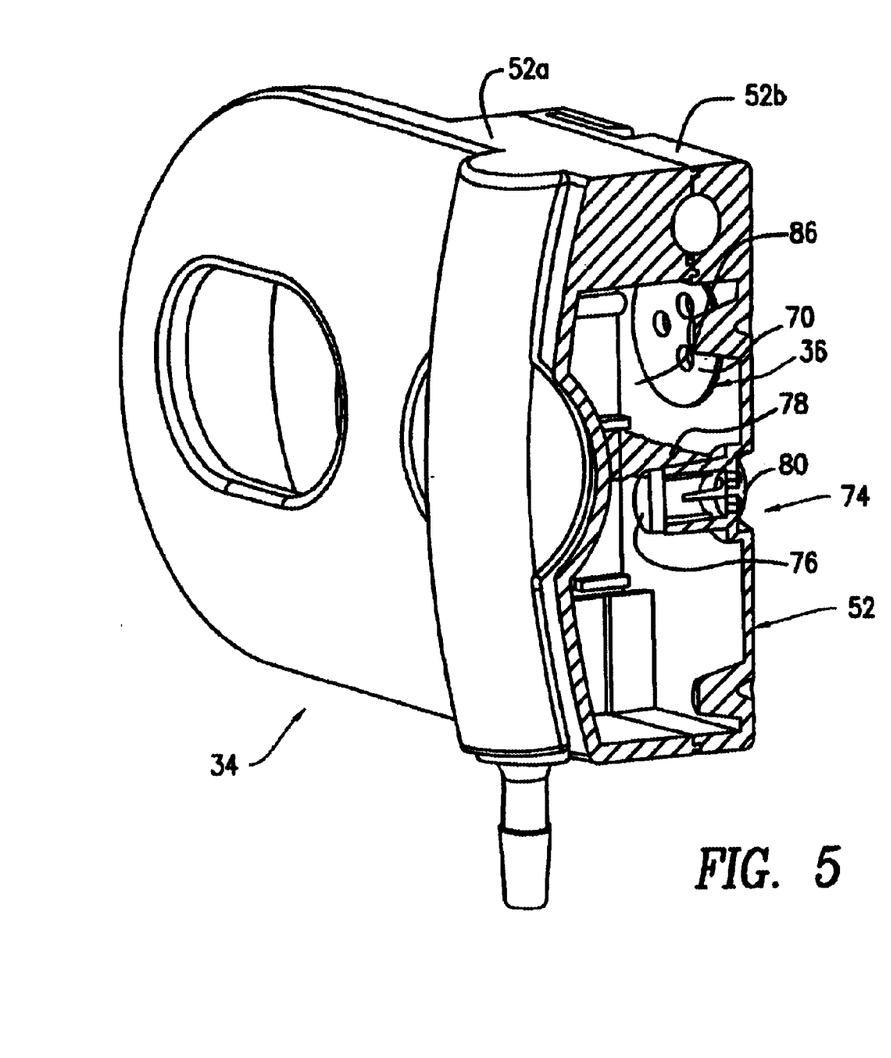
FIG. 5 is a cross-sectional view of the flow dampener of FIG. 3 taken along section lines V—V and looking in the direction of the arrows.

FIG. 5 shows a first dampener 34 embodiment with an air vent 74 for maintaining a predetermined fluid level within the pressure chamber 52. A hydrophobic micropore filter 76 permits air to flow therethrough allowing the fluid 78 level to rise to just cover the hydrophobic filter 76. A one way valve 80, e.g., a mushroom valve, prevents air from entering the pressure chamber 52 in response to negative pressure therein. The fluid 78 traps a pocket of air 86 thereabove, with gravity maintaining this stratified air/fluid separation. The pocket of air 86 exhibits the expected pressure/volume relationship at room temperature in accordance with Boyle's law. With increased fluid input, the air pocket 86 becomes pressurized and this pressure is transmitted to the pressure sensor 36 (i.e., the pressure sensing diaphragm 70). Because the air pocket 86 is compressible, unlike the fluid 78, variations in output volume from the pump 32 (i.e., due to turning rollers 66 which sequentially squeeze down upon the unshaped section 64) are smoothed by the air pocket 86, which acts like a cushion. More specifically, the fluid exiting the pressure chamber 52 is propelled therefrom by the pressure prevailing in the air pocket 86. Small variations in pump 32 output volume to the pressure chamber 52 do not cause significant variations in pressure in the air pocket 86. As a consequence, fluid output from the pressure chamber 52 is more constant. The air pocket 86 also retains gases that are contained in the fluid, thereby avoiding pumping gases in the fluid to the surgical site.

Figure 6:
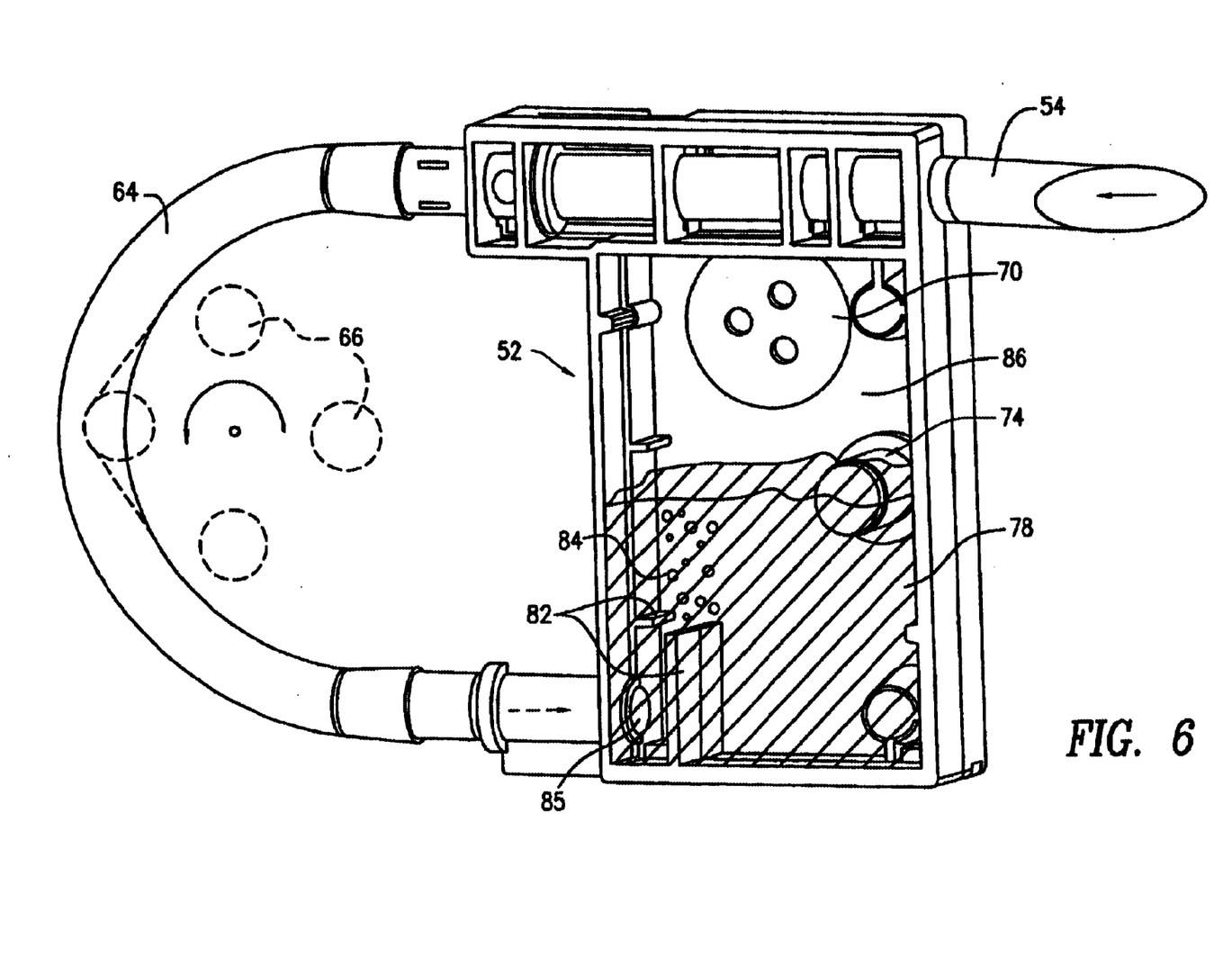
FIG. 6 is a cross-sectional view of the flow dampener of FIG. 4 taken along section lines VI—VI and looking in the direction of the arrows.

FIG. 6 shows the interaction of the rollers 66 of a peristaltic pump 32 with the u-shaped section 64 of tubing, such interaction inducing a flow of fluid in the direction of the arrows shown. Specifically, fluid flows into the inlet tube 54 and through the u-shaped section 64 into the pressure chamber 52. A pair of baffles 82, 84 are shown positioned around a fluid inlet 85 of the pressure chamber 52. The baffles 82, 84 induce a fluid flow in an upward direction and prevent the in-flowing fluid to flow out the outlet directly, thereby permitting air or other gases entrained in the fluid to rise through the fluid 78 into the upper portion of the pressure chamber 52 (i.e., into the air pocket 86).

Figure 7:
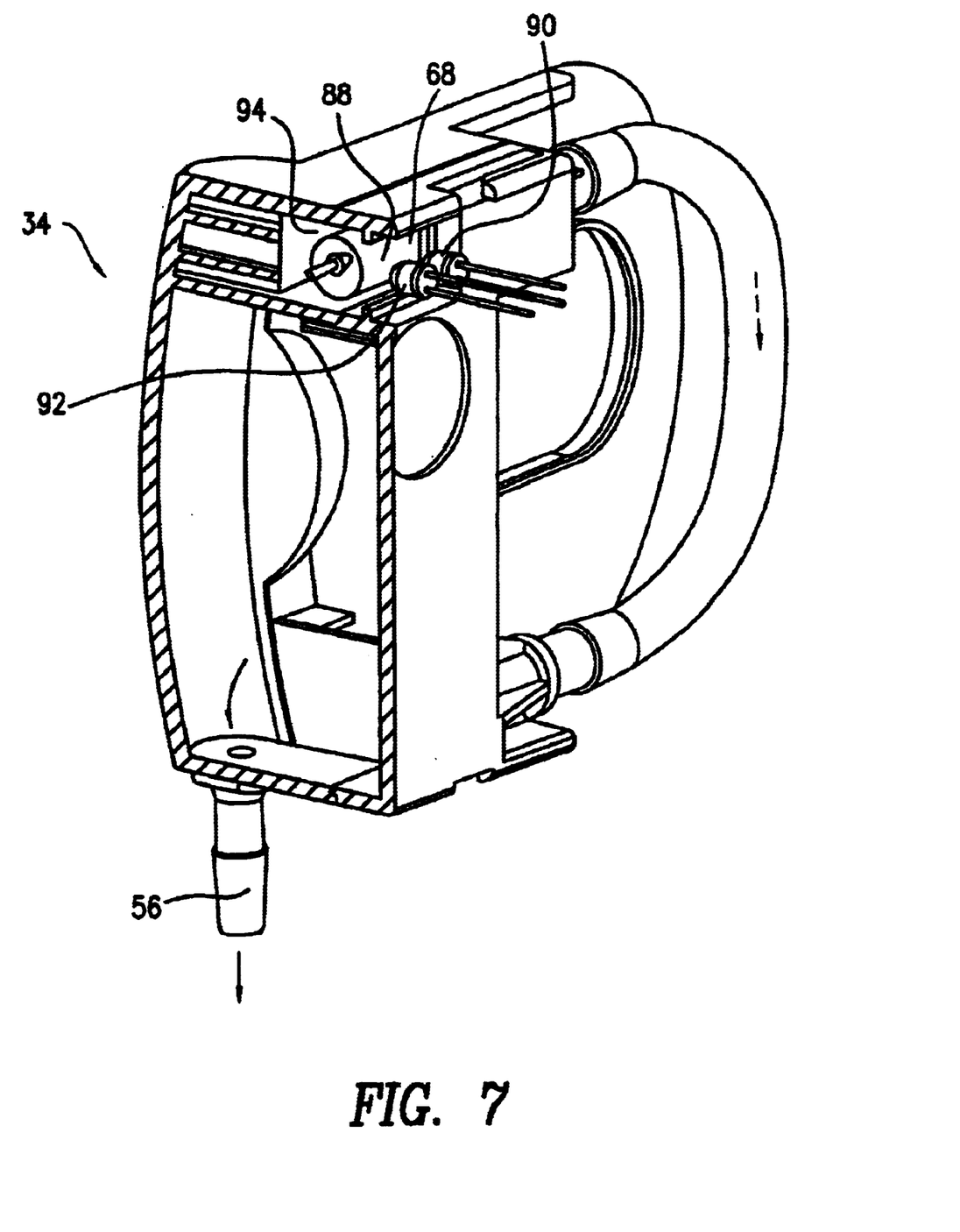
FIG. 7 is a cross-sectional view of the flow dampener of FIG. 4 taken along section lines VII—VII and looking in the direction of the arrows.

FIG. 7 shows how a flow sensor 38 (see FIG. 2) may be incorporated into the flow dampener 34 of the present invention. More particularly, a light-emitting element 90, such as a light bulb or LED, is positioned proximate to the light detection window 68. The light emitted by the element 90 is transmitted through the light-transmissive tubing 88 and strikes a reflective surface or mirror 94 on the other side of the tubing 88. Light reflected from the mirror 94 is retransmitted through the tubing 88 and strikes a light-sensing element 92, such as a photodiode or phototransistor, that converts the incoming light signal to a voltage level or current flow.

Figures 8, 9:
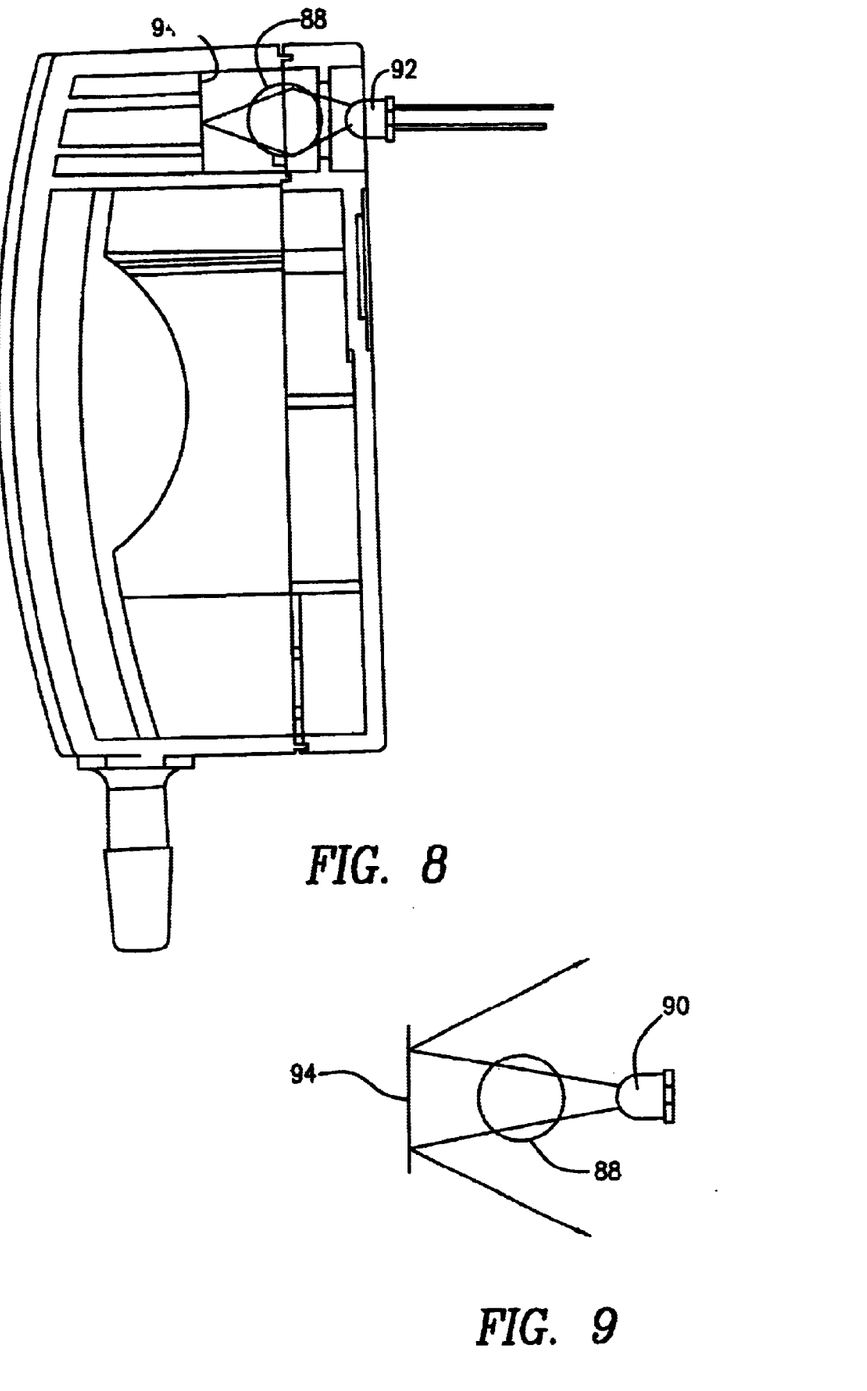
FIG. 8 is an end-on view of the cross-section of the flow dampener shown in FIG. 7.
FIG. 9 is a diagrammatic view of light transmitted through an empty tube and reflected from an adjacent reflective member.

Referring to FIGS. 8 and 9, one can appreciate how the foregoing light sensing arrangement will operate, namely, that light emitted by the element 90 will pass through the tubing 88, if it is empty, in a diffuse manner and will strike the mirror 94 and diffuse even further, such that the return signal to the light-sensing element 92 will be weak (see FIG. 9). In contrast, if the tubing 88 is filled with fluid as shown in FIG. 8, it will act as a lens, focusing the light signal from the light-emitting element 90 on the reflective surface 94 such that the signal retransmitted from the mirror 94 will be likewise focused on the light-sensing element 92 and will have a much greater magnitude than if the tubing 88 were empty. The light signal received at the light-sensing element 92 can then be processed by suitable circuitry, e.g., like that shown in FIG. 10, to interpret the variation in light magnitude to indicate the presence of fluid in the tubing 88 or the lack of fluid.

Figure 10:
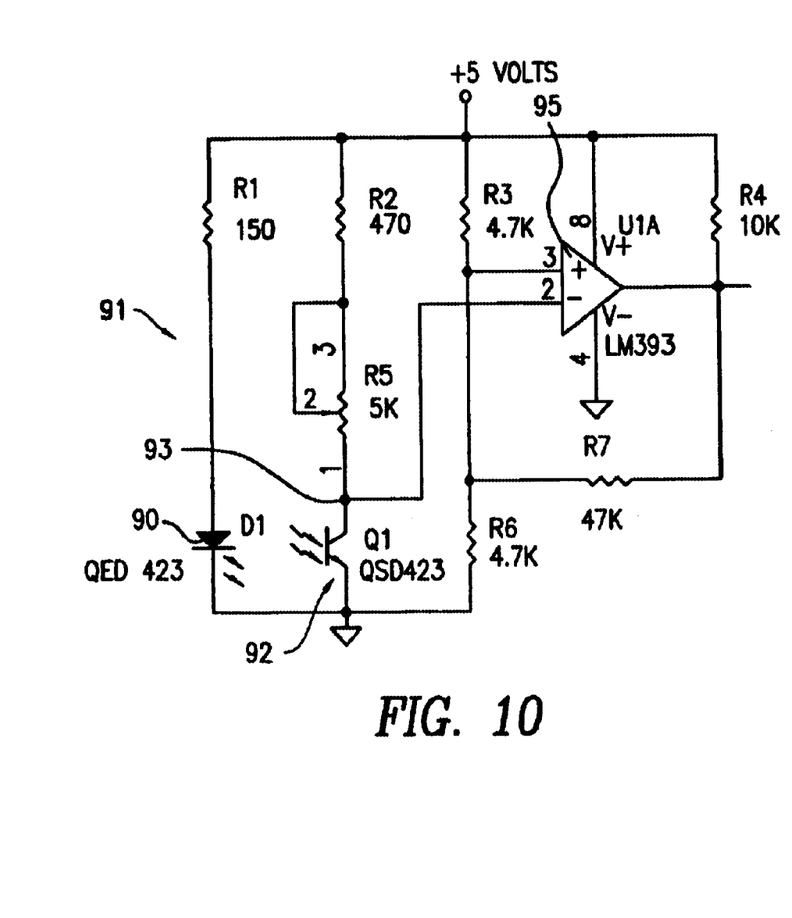
FIG. 10 is a circuit diagram for an optical sensor in accordance with the present invention.

FIG. 10 shows a circuit 91 having a light-emitting element 90 (in the form of a light-emitting diode) and a light-sensing element 92 (in the form of a phototransistor), which would by physically juxtaposed as shown in FIG. 7. The voltage at point 93 will vary depending on the current flow through the light-sensing element (i.e., phototransistor) 92 as determined by the presence or absence of fluid in tubing 88 (see FIG. 7) and the corresponding magnitude of light transmitted to the light-sensing element (i.e., phototransistor) 92. The voltage level at 93 is compared with a reference voltage and the difference amplified by operational amplifier 95, the output of which is the signal representing the presence or absence of fluid in the tubing 88.

Figure 11:
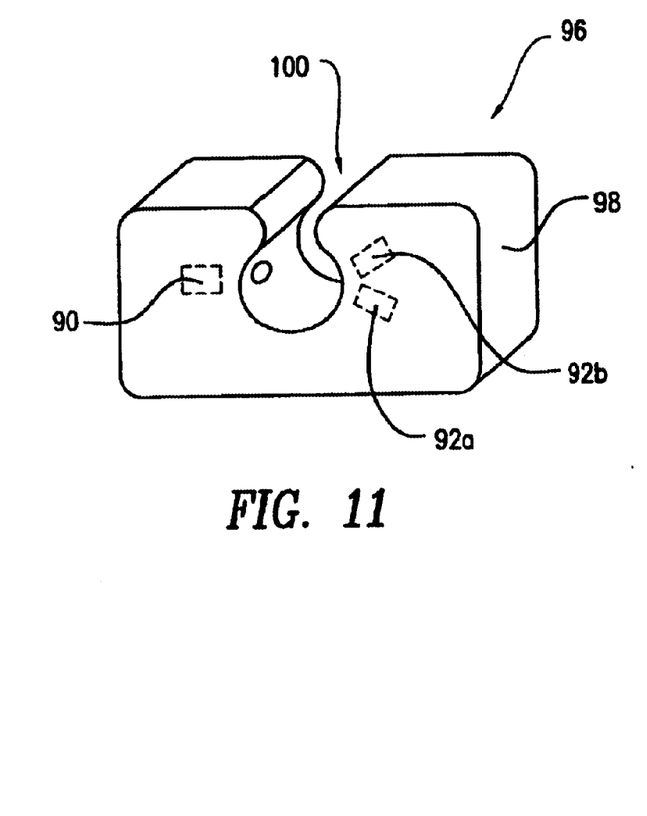
FIG. 11 is a perspective view of an optical fluid sensor in accordance with a second embodiment of the present invention.

FIG. 11 shows an alternative embodiment for a fluid detector 96 in accordance with the present invention which includes a body 98 having a tube receptacle 100 formed therein. The tube receptacle 100 slidably receives a tube (not shown) which can be flattened slightly and inserted into the narrowed portion of the tube receptacle 100 and then allowed to relax and assume its normal cylindrical shape. As before, a light-emitting element 90 can be placed on one side of the tubing. In this embodiment however, rather than having a single photodetector and circuitry to distinguish between two light magnitudes associated with the presence or absence of fluid in the tube, there are two light-sensing elements 92a, 92b spatially separated such that if a diffuse transmission of light through the tube results, namely if the tube is empty, then both of the spaced light-sensing elements 92a, 92b will receive the light transmission. Otherwise, if the transmission is focused due to the presence of fluid in the tube, then only the light-sensing element 92b will be exposed to the light transmission. The signals received by the light-sensing elements 92a, 92b can be compared, amplified, etc. in order to convey a signal indicative of the presence or absence of fluid in a tube about which the detector 96 is positioned.

Figure 12:
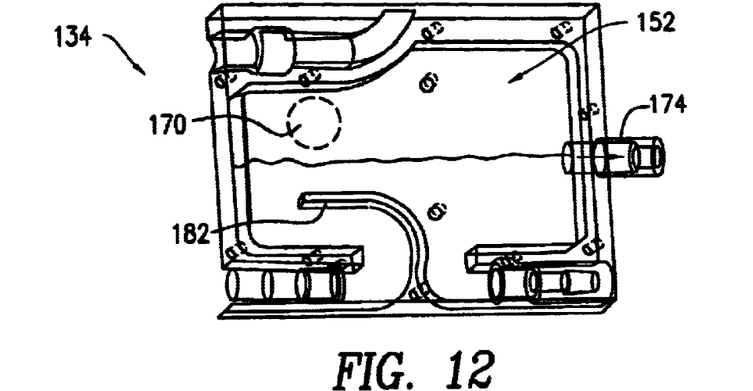
FIGS. 12–14 are cross-section views of second, third and fourth embodiments of the flow dampener of the present invention.
Figure 13:
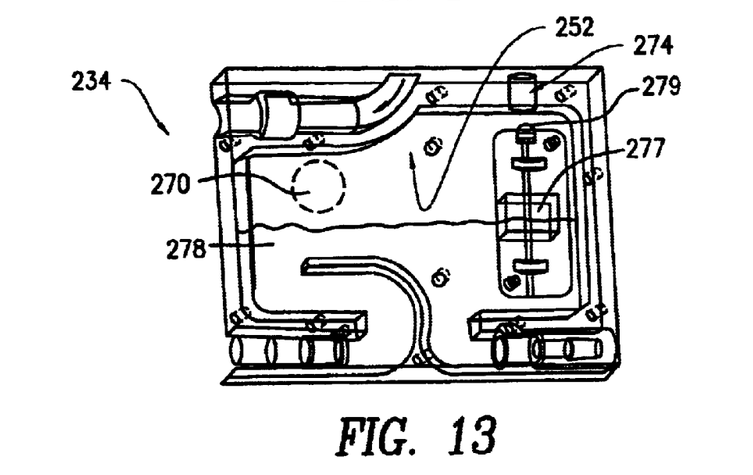
Figure 14:
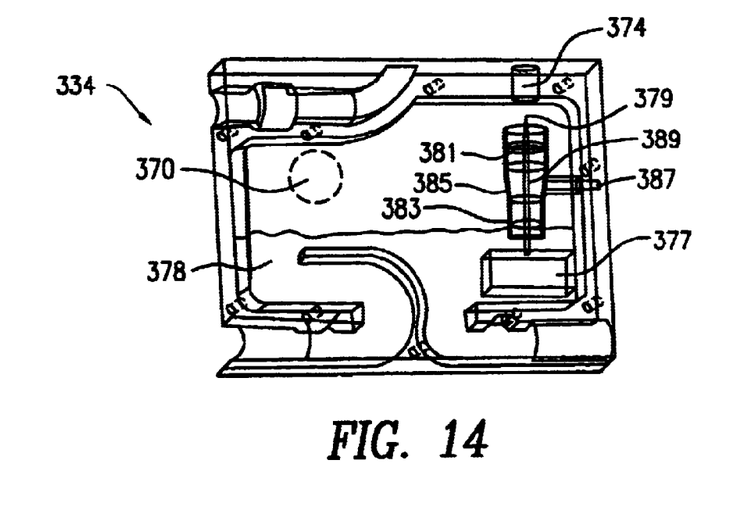

FIGS. 12, 13 and 14 show variations of the flow dampener 34 described above, with FIG. 12 having a modified baffle 182 which causes the input flow to reverse direction. As before, a hydrophobic micropore filter 174 determines fluid level in the pressure chamber 152.

In FIG. 13, the hydrophobic micropore filter of the previous embodiments has been replaced by an upper air vent orifice 274 which is stoppered and unstoppered depending upon the fluid level 278 within the pressure chamber 252 which lifts float 277 and plug 279 to close the air vent 274.

In FIG. 14, the hydrophobic micropore filter has been replaced with an air vent 374 that is controlled by a needle valve 379, the position of which is responsive to fluid level 378 which urges float 377 up and down. In FIG. 14, the buoyancy of float 377 is counterbalanced by a pair of pistons 381, 383, each having different cross-sectional areas and thereby applying different counteracting forces on a shaft 389 that couples the pistons 381, 383 and attaches to the float 377. A common cylinder sleeve 385, which includes upper and lower mating cylinder bores, vents centrally to the atmosphere via a vent 387.

Turning now to the suction side of the system 30, one will recall that in a conventional fluid management systems vacuum control like the one shown in FIG. 1, a mechanical vacuum regulator regulates a pressure common to multiple fluid receptacles, i.e., those going to the fluid receptacles 24', 26', as well as to the drape system 28'. Frequently, the large volume of flow attributable to the drape system 28' overpowers the common regulator dropping the vacuum level to the fluid receptacles 24', 26' until the drape suction is turned off. This situation is compounded by the fact that vacuum regulators are sometimes ineffective in supplying a well-regulated high volume flow and often vent very slowly if the vacuum is too high. In conventional systems, the vacuum level is sensed at the regulator, therefore vacuum drops through the flow-back filter 22', the receptacles 24', 26' and their associated tubing are not compensated for in regulating the vacuum.

Figure 15:
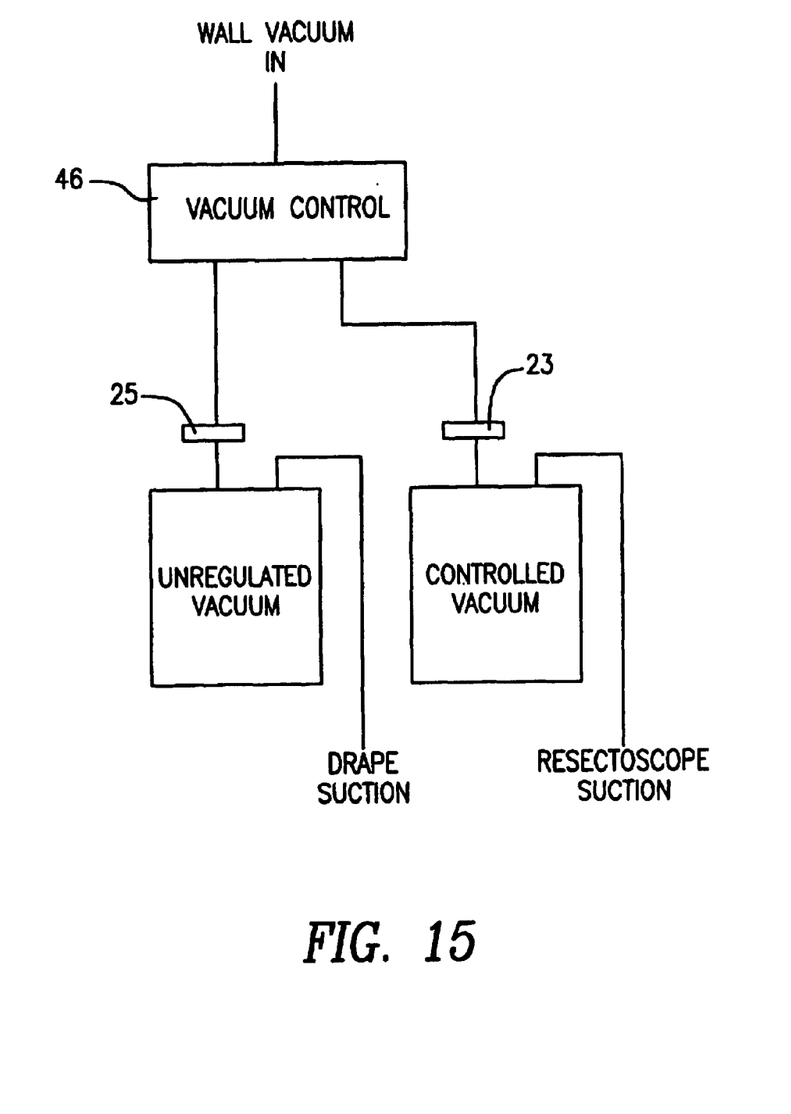
FIG. 15 is a schematic diagram showing the relationship between elements in a vacuum control system in accordance with the present invention.

FIG. 15 diagrammatically shows that the vacuum controller 46 of the present invention provides controlled vacuum to the body cavity 12 (resectoscope suction), be uncontrolled vacuum to the surgical drape where maintenance of controlled vacuum is less critical. The present invention thus utilizes prioritized vacuum sharing wherein the vacuum controller 46 maintains a regulated vacuum in the fluid receptacles 24,26 connected to the resectoscope. Any remaining vacuum is routed to the drape suction once sufficient vacuum is directed to the fluid receptacles 24, 26. This eliminates the problem of an open drape suction overpowering the ability to maintain a good regulated vacuum. The valve means for performing the foregoing are described below in reference to FIGS. 16 and 17.

Figure 16:
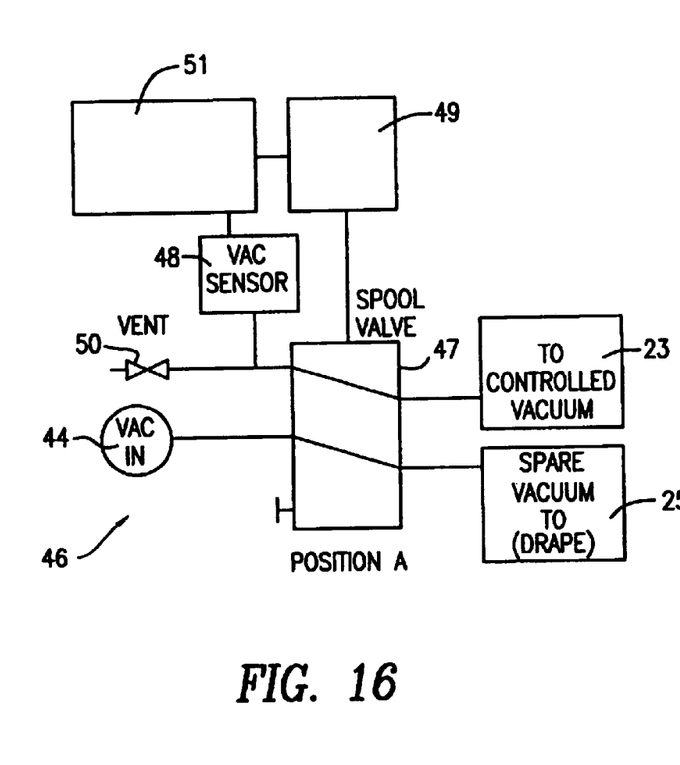
FIGS. 16 and 17 are schematic diagrams showing a spool valve in two different states of distributing and measuring vacuum in a fluid management system in accordance with the present invention.
Figure 17:
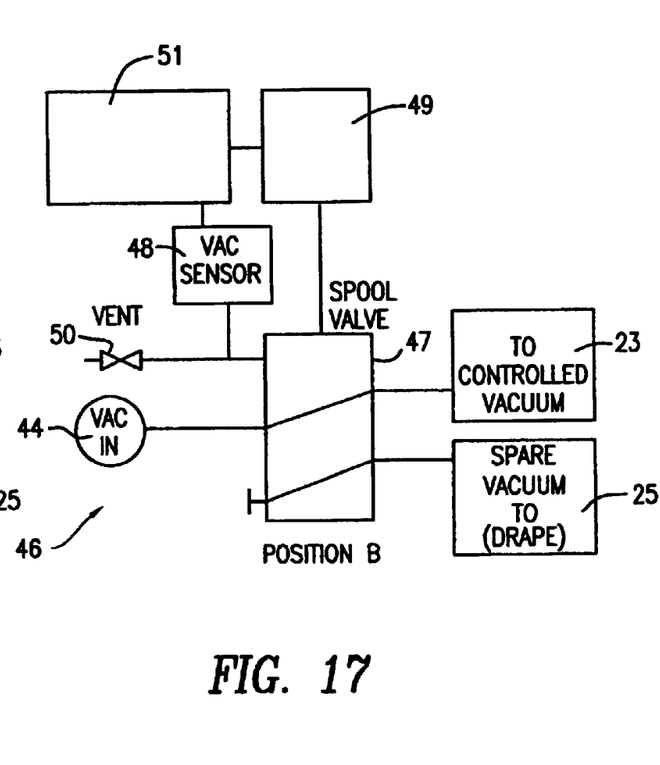

FIGS. 16 and 17 show the vacuum controller 46 equipped with a high capacity spool valve 47 actuated by actuator 49 under the control of microprocessor 51 based upon signals representing vacuum magnitude received from the vacuum sensor 48.

In position A shown in FIG. 16, the controlled vacuum outlet is connected to the vacuum sensor 48 and the vent valve 50. The vacuum appearing at regulator valve 44 is connected to the spare vacuum output connected to the flow-back filter 25 leading to the drape. If the vent valve 50 is open in this position, it will vent the controlled vacuum. If the vent valve 50 is closed, the vacuum sensor 48 can measure the vacuum in the controlled vacuum receptacles 24, 26 with no flow and therefore no erroneous vacuum readings. The present invention recognizes the fact that when vacuum is applied to the receptacles 24, 26, there is significant pressure drop through the flow-back filter 23 and the tubing to the receptacles 24, 26. The present invention samples the vacuum pressure only when the flow is stopped so that the vacuum controller 46 can operate based on a more accurate vacuum reading.

In position B shown in FIG. 17, the controlled vacuum outlet is connected to the vacuum appearing at regulator valve 44. The vacuum sensor 48 and the spare vacuum to the flow-back filter 25 leading to the drape are blocked. In this position, vacuum in the receptacles 24, 26 and heading to the cavity 12 increases.

To control the level of vacuum evacuating the fluid from the cavity 12, a software algorithm in microprocessor 51 switches the spool valve 49 between position A and position B periodically, e.g., once per second. The amount of time the valve 47 is in position B, supplying vacuum to the controlled receptacles 24, 26, is based upon the last vacuum measurement made in position B. By observing the change in vacuum level from one measurement to the next in relationship to how long the spool valve 47 was last held in position B, the software can determine how long to next hold the spool valve 47 in position B to achieve and maintain a given vacuum level in the controlled vacuum receptacles 24, 26.

The low restriction spool valve 47 allows quick changes in the vacuum level in the controlled vacuum receptacles 24, 26. The inclusion of the vent valve 50 makes increasing the pressure (bleeding off vacuum) quick as well. This relationship is depicted graphically in FIG. 18.

Figure 18:
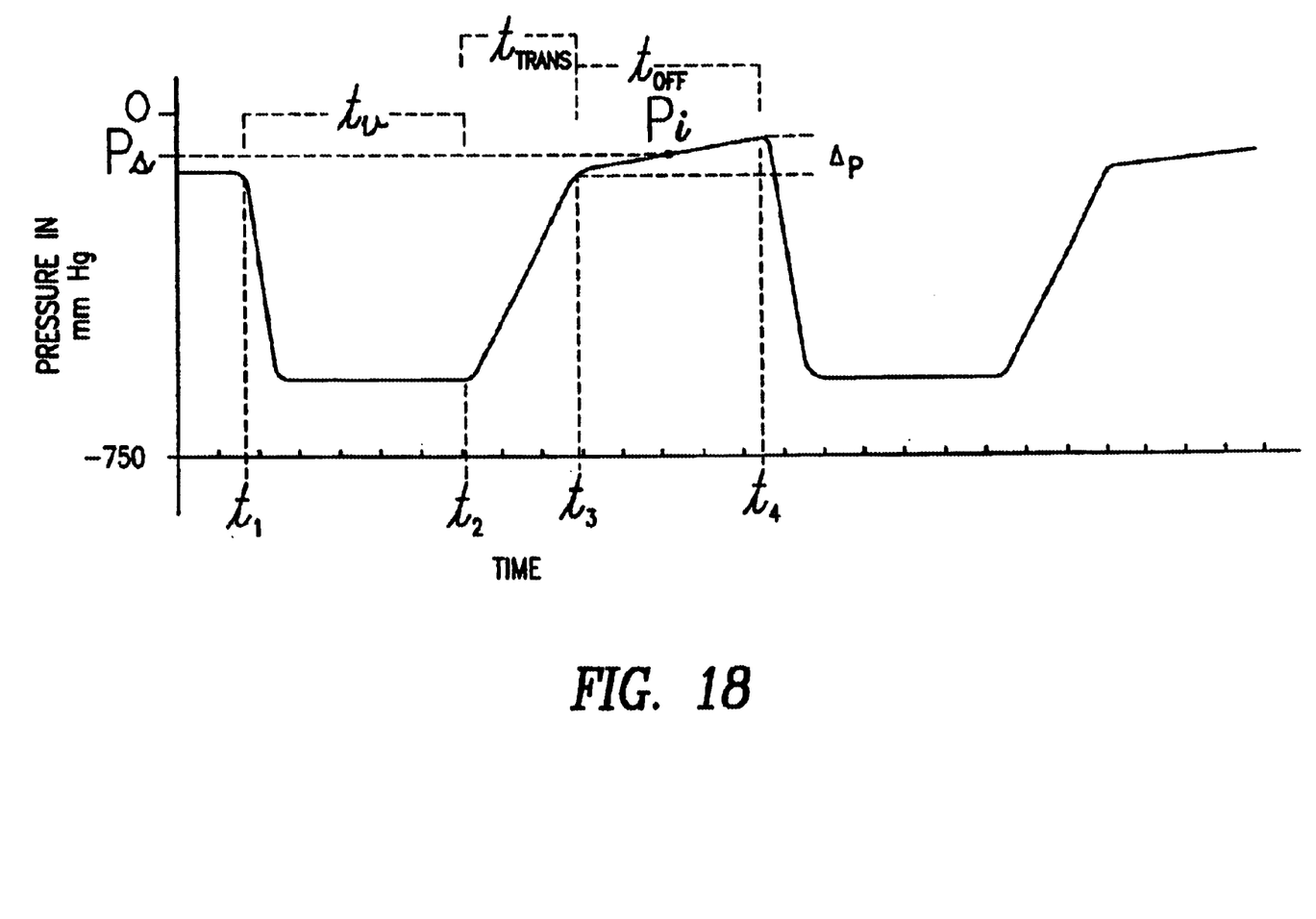
FIG. 18 is a graph of pressure vs. time exhibited by a fluid management system in accordance with the present invention.

FIG. 18 shows the vacuum present in the receptacle 26 as a function of time and as a result of the intermittent connection of the flow-back filter 23 to the vacuum source 18 via the vacuum controller 46 and more specifically the spool valve 47. At time $t_1$, the spool valve 47 is placed in position B (see FIG. 17), whereupon the vacuum directed to cavity 12 increases rapidly (drop in pressure). The spool valve 47 is held in position B until time $t_2$, when it is cycled to position A (see FIG. 16). Time period $t_1$ to $t_2$ can be described as the time the cavity 12 suction is exposed to input vacuum or $t_v$. The change of position of the spool valve 47 from position B to position A is not instantaneous but rather occurs over a transition period $t_{trans}$ extending from time $t_2$ to $t_3$. Once the spool valve 47 is in position A at $t_3$, the vacuum present in elements (i.e., the flow-back filter 23 and the reservoirs 24, 26) between the spool valve 47 and the cavity 12 can stabilize during the period from $t_3$ to $t_4$ when the spool valve 47 remains in position A. The time period from $t_3$ to $t_4$ when the vacuum source 18 is isolated from the flow-back filter 23 may be called $t_{off}$. During $t_{off}$ a vacuum drop (raise in pressure) Δp is experienced. The foregoing process is repeated cyclically such that the number of complete cycles from $t_1$ to $t_4$ over a reference time period is the frequency. The objective then is to vary the pulse widths representing the times when the spool valve 47 is alternately in positions B and A so that the approximate average or intermediate pressure $P_i$ during $t_{off}$ approximates the set point pressure $P_s$. This can be accomplished under algorithmic control by interactively measuring the vacuum and adjusting $t_v$ such that $P_i$ approximates $P_s$.

System capacity varies depending upon the number of receptacles 24, 26 chained together and the level of fluid fill in each. Thus, the relationship between $t_v$ and Δp varies as the case proceeds. The control loop evaluates the ratio of Δp/$t_v$ and uses this in a difference equation to compute the next $t_v$ in order to achieve a desired vacuum level. The slope of vacuum drop over time $t_{off}$ is a measure of air flow. The control algorithm preferably maintains a maximum Δp difference within some minimum valve cycle time.

The variable $t_v$ is computed based on the last observed Δp and the desired Δp. A pulse may be skipped to vent vacuum. Maximum $t_v$ must be less than the repetition rate so that Δp can be measured, i.e., a minimum $t_{off}$ time is required at least once per/period. Once $t_{off}$ is at minimum, the vacuum flow is maxed out.

It should be understood that the embodiments described herein are merely exemplary and that a person skilled in the art may make many variations and modifications without departing from the spirit and scope of the invention as defined in the appended claims.

What is claimed is:

1. Apparatus for controlling a volume of surgical fluid present in a cavity in a body of a patient during a surgical procedure that employs a surgical drape to catch waste surgical fluid, comprising:

a first conduit to the cavity for conducting the surgical fluid therefrom;

a first receptacle for receiving the surgical fluid from the cavity, said first conduit communicating with said first receptacle;

a second conduit to the surgical drape for conducting the waste surgical fluid therefrom;

a second receptacle for receiving the waste surgical fluid from the drape, said second conduit communicating with said second receptacle;

a vacuum source;

a valve having at least two positions and interposed between said first receptacle and said vacuum source and between said second receptacle and said vacuum source, a vacuum controller with a microprocessor controlling the position of said valve and alternatingly switching said valve between a first position connecting said first receptacle to said vacuum source and a second position connecting said second receptacle to said vacuum source, said vacuum controller controlling the duration of time said first receptacle and said second receptacle are exposed to a vacuum from said vacuum source, the vacuum rom said vacuum source being shared between said first receptacle and said second receptacle by sequential timed distribution thereof by said valve alternately switching between said first position and said second position under the control of said valve controller, said sharing of vacuum being prioritized by an algorithm executed by said microprocessor to favor the acquisition of a setpoint vacuum level in said first receptacle over the application of vacuum to said second receptacle;

a vacuum sensor for sensing a vacuum level approximating that in said first receptacle; and a timer for measuring the time that said valve is maintained in said first position and in said second position, respectively, said vacuum controller controlling a duration of time said frist receptacle is exposed to vacuum based upon data from said vacuum sensor, said vacuum controller comparing the data from said vacuum sensor to a preselected vacuum setpoint and adjusting the time of exposure up or down as required to achieve the preselected vacuum setpoint, said valve having a first port connected to said vacuum source, a second port connected to said first receptacle, a third port connected to said vacuum sensor and a fourth port connected to said second receptacle, said first port and said second port being connected when said valve is in the first position, said second port and said third port being connected when said valve is in the second position and said first port and said fourth port being connected when said valve is in the second position.

2. The apparatus of claim 1, wherein said valve is a spool valve.

3. The apparatus of claim 1, wherein said first receptacle includes a plurality of receptacles connected together by means for conveying fluid thereto.

4. The apparatus of claim 1, further comprising a flowback filter positioned between said vacuum controller and said first receptacle.

5. The apparatus of claim 1, further comprising a pump for supplying surgical fluid to the cavity.

6. The apparatus of claim 5, wherein said pump is adjustable to provide a selected output based upon a pressure approximating that present in the cavity.

7. The apparatus of claim 6, further including a dampener disposed between said pump and the cavity, said dampener receiving the fluid output of said pump and having pressure-sensitive volumetric capacity such that variations in output volume of said pump are diminished by said dampener, the output of which is directed to the cavity.

8. The apparatus of claim 7, further including a fluid sensor for sensing the presence of the surgical fluid that is directed to the cavity by said pump.

9. The apparatus of claim 8, wherein said fluid sensor includes a light emitting element and a light detector, said light detector juxtaposed proximate said light emitting element to receive light passing through a light transmissive portion of a supply conduit through which the surgical fluid flows before entering the cavity, with light received by said light detector varying depending upon the presence or absence of fluid in said light transmissive portion, such variation in light received being converted by said light detector into an electrical signal that is interpreted to determine the presence or absence of fluid in said light transmissive portion.

10. The apparatus of claim 1, wherein said vacuum sensor is in communication with a vent valve, said vent valve venting off vacuum when in an open position.

11. The apparatus of claim 10, wherein said vent valve has a vent actuator in communication with said vacuum controller permitting said vacuum controller to move said vent valve between said open position and a closed position.

* * * * *